United States Patent
Adams et al.

(10) Patent No.: US 12,291,510 B2
(45) Date of Patent: May 6, 2025

(54) 2,5-DIMERCAPTO-1,3,4-THIADIAZOLE (DMTD) DERIVATIVES

(71) Applicant: The Lubrizol Corporation, Wickliffe, OH (US)

(72) Inventors: Paul E. Adams, Willoughby, OH (US); Christopher M. Rasik, Cleveland, OH (US); Ryan Richard Konrad, Timberlake Village, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 547 days.

(21) Appl. No.: 17/760,830

(22) PCT Filed: Sep. 16, 2020

(86) PCT No.: PCT/US2020/050947
§ 371 (c)(1),
(2) Date: Mar. 16, 2022

(87) PCT Pub. No.: WO2021/055388
PCT Pub. Date: Mar. 25, 2021

(65) Prior Publication Data
US 2022/0380326 A1    Dec. 1, 2022

Related U.S. Application Data

(60) Provisional application No. 62/901,312, filed on Sep. 17, 2019.

(51) Int. Cl.
*C07D 285/125*    (2006.01)

(52) U.S. Cl.
CPC .............................. *C07D 285/125* (2013.01)

(58) Field of Classification Search
CPC .......................... C07D 285/125; C07D 417/12
See application file for complete search history.

(56) References Cited

U.S. PATENT DOCUMENTS

| | | | |
|---|---|---|---|
| 4,772,546 A | 9/1988 | Deguchi et al. | |
| 4,855,310 A * | 8/1989 | Murase | C07D 249/04 514/363 |
| 5,414,090 A | 5/1995 | Love et al. | |
| 6,340,539 B1 | 1/2002 | Yamaguchi et al. | |
| 6,489,484 B1 | 12/2002 | Karol et al. | |
| 2002/0058594 A1 | 5/2002 | Karol et al. | |
| 2005/0191589 A1 | 9/2005 | Loccufier et al. | |
| 2006/0168741 A1 | 8/2006 | Laufer et al. | |
| 2009/0156444 A1 | 6/2009 | Aguilar et al. | |
| 2018/0097248 A1 | 4/2018 | Nariyama et al. | |
| 2019/0020031 A1 | 1/2019 | Otsuka | |

FOREIGN PATENT DOCUMENTS

| | | |
|---|---|---|
| JP | H05127295 A | 5/1993 |
| JP | 2013234126 A | 11/2013 |
| WO | 01/29155 A2 | 4/2001 |
| WO | 01/29156 A2 | 4/2001 |

OTHER PUBLICATIONS

Katritzky, Alan R., et al., S,S'- and S,N-Disubstituted Derivatives of 1,3,4-Thiadiazoledithiones, J. Heterocycle Chem., vol. 27, Feb. 1990, pp. 139-142.

American Chemical Society, STN, Registry, No. 4887-26-7, CAS SciFinder, Jul. 9, 2001.

* cited by examiner

*Primary Examiner* — Laura L Stockton
(74) *Attorney, Agent, or Firm* — Christopher P. Demas; Michael A. Miller

(57) ABSTRACT

The disclosed technology relates to derivatives of 2,5-dimercapto-1,3,4-thiadiazole.

1 Claim, No Drawings

2,5-DIMERCAPTO-1,3,4-THIADIAZOLE (DMTD) DERIVATIVES

CROSS REFERENCE TO RELATED APPLICATION

This application claims priority from PCT Application No. PCT/US20/050947 filed on Sep. 16, 2020, which claims the benefit of U.S. Provisional Application No. 62/901,312 filed on Sep. 17, 2019, the entirety of which is hereby incorporated by reference.

BACKGROUND OF THE INVENTION

The disclosed technology relates to derivatives of 2,5-dimercapto-1,3,4-thiadiazole.

Some simple alkyl and aryl substituted DMTD derivatives are known, for example, as taught in U.S. Pat. No. 2,736,729, granted Feb. 28, 1956 to Krzikalla et al. and U.S. Pat. No. 3,212,892, granted Oct. 19, 1965, to von Konig et al. Simple acrylic acid alkyl and aryl esters of DMTD are also known, for example, as taught in JP 2013234126, published Nov. 21, 2013 to Oya et al., and U.S. Pat. No. 5,258,395, granted Nov. 2, 1993 to Murase et al.

New chemistries are needed that can readily change oxidation states and are based on organic chemistry. Examples of such chemistry in the art usually start with some or all of relatively expensive starting materials and reagents, may need multiple steps to obtain the target final product, generate large quantities of undesirable process wastes, and could also require tedious purification steps.

SUMMARY OF THE INVENTION

The disclosed technology, therefore, solves the problem of difficult to produce and expensive but readily oxidizable organic chemistry by providing new DMTD derivatives that are synthesized in only one or two steps, starting from readily available and inexpensive raw materials, use processing that generates little or no waste, and involve reactions which proceed rapidly and in high product conversions.

One aspect of the technology is directed to a DMTD derivative obtained as the reaction product of: a) 2,5-dimercapto-1,3,4-thiadiazole ("DMTD"), and b) at least one of: i) halo-ether group, ii) a halo-alcohol group, iii) an epoxide group, iv) a carboxamide group, and v) carboxylate group.

In embodiments, any of the foregoing DMTD derivatives can be further reacted with a base. Similarly, any of the foregoing DMTD derivatives can be further reacted with an oxidizing reagent.

The foregoing reaction products can include a mono-ether DMTD derivative, in a salt form or not, or as a sulfur coupled bis-compound.

The foregoing reaction products can include a mono-alcohol DMTD derivative, in a salt form or not, or as a sulfur coupled bis-compound.

The foregoing reaction products can include a mono-carboxamide DMTD derivative, in a salt form or not, or as a sulfur coupled bis-compound.

The foregoing reaction products can include a mono-carboxylate DMTD derivative, in a salt form or not, or as a sulfur coupled bis-compound.

Another aspect of the technology is directed to a DMTD derivative obtained as the reaction product of: a) 2,5-dimercapto-1,3,4-thiadiazole ("DMTD"), and b) at least one of a: i) a halogenated hydrocarbyl group, and ii) (meth)acrylate group, and c) an oxidizing agent.

The foregoing reaction products can include a mono-alkyl bis-DMTD derivative. The foregoing reaction products can also include a mono-(meth)acrylate bis-DMTD derivative.

Another aspect of the technology is directed to a zwitterionic DMTD derivative obtained as the reaction product of: a) 2,5-dimercapto-1,3,4-thiadiazole ("DMTD"), and b) at least one of: i) a linear, branched, saturated or unsaturated, cyclic halogenated $C_1$ to $C_{22}$ alkyl or aryl quaternary ammonium group, ii) a quaternary ammonium containing halo-ether group, iii) a quaternary ammonium containing halo-alcohol group, iv) a quaternary ammonium containing epoxide group, v) a quaternary ammonium containing carboxylate group, and vi) a quaternary ammonium containing carboxamide group, and c) a strong base.

The foregoing reaction products can include a zwitterionic mono-quaternary ammonium containing alkyl DMTD derivative.

The foregoing reaction products can include a zwitterionic mono-quaternary ammonium containing ether DMTD derivative.

The foregoing reaction products can also include a zwitterionic mono-quaternary ammonium containing alcohol DMTD derivative.

The foregoing reaction products can include a zwitterionic mono-quaternary ammonium containing (meth)acrylamide DMTD derivative.

The foregoing reaction products can include a zwitterionic mono-quaternary ammonium containing (meth)acrylate DMTD derivative.

DETAILED DESCRIPTION OF THE INVENTION

Various preferred features and embodiments will be described below by way of non-limiting illustration.

Provided herein are derivatives of 2,5-Dimercapto-1,3,4-thiadiazole ("DMTD"). The DMTD derivatives include reaction products of DMTD and other chemical reagents via a variety of different chemical reactions. These reactions include displacements using electron deficient hydrocarbons, 1,4-additions to olefins, and epoxide opening reactions, as well as acid-base reactions and disulfide formation (processes and co-reactants/catalysts for which are known in the art and readily envisage by those of ordinary skill). These reactions can be performed in the presence of a wide array of functional groups that can provide for desired solubility and electrochemical performance. These functional groups include carbonyl-containing molecules, heteroatom-containing molecules (nitrogen, oxygen, sulfur), inorganic atoms, and unsaturation.

While the reaction products to prepare the derivatives often result in a mixture of products, the products can be provided as pure compounds as well. In general, the DMTD derivatives can be represented in the pure form by formula I:

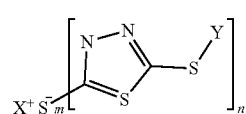

Formula I where each "X" individually, is an alkali or alkaline earth metal, such as Li, Na, K, Mg, or Ca, a trialkyl amine, or a quaternary amine (including for purposes of this disclosure, ammonia), or H;

"m" is 1, 2 or 3, and "n" is 1 or 2; and where "Y" is:

"$[RO]_oR$," where "o" is an integer from 1 to 100;

"$R[OH]_pA$," where "p" is an integer from 1 to 6 and "A" is H or an amine, such as a trialkyl amine or a quaternary amine salt;

a carboxamide, such as a (meth)acrylamide of "$CH_2CH[CH_3$ or $H]C(O)NHZ$," where "Z" is H, "R," "$RSO_3^-Na^+$," "$RSO_3H$," or "$RN^+(R)_3Cl^-$," or a carboxylate, such as an itaconate, maleate, or, for example, a (meth)acrylate of "$CH_2CH[CH_3$ or $H]C(O)OZ$," where "Z" can be X, $RN^+(R)_3SO_3^-$, $RN^+(R)_3SO_3^-K^+$, "$RSO_3^-Na^+$," $RSO_3^-NH_4^+$, "$RSO_3H$," or "$RN^+(R)_3Cl^-$," and where "R" is a linear, branched, saturated or unsaturated, or cyclic $C_1$ to $C_{12}$, or $C_1$ to $C_{10}$, or $C_1$ to $C_8$, or even $C_1$ to $C_6$ alkyl or aryl group, or H.

Examples of the R group can include methyl, ethyl, propyl, butyl, pentyl, hexyl, heptyl, octyl, nonyl, decyl, undecyl, and dodecyl groups, including branched versions thereof, such as, for example, isobutyl, ethylhexyl, isoamyl, and the like, as well as aromatic groups (e.g. benzyl, phenyl, tolyl, xylyl, naphthyl, etc.) or cyclic groups (e.g., cyclohexyl).

In preparing the DMTD derivatives, a base may be employed. Such a base may be, for example, an alkaline or alkaline earth metal hydroxide or carbonate, or an amine, such as, for example a trialkyl amine. If a base is employed, "X" in the foregoing formulas can be an alkali or alkaline earth metal such as Li, Na, K, Mg, or Ca, or a trialkyl amine. If a base is not employed, "X" would be H and the positive and negative charges associated therewith would be absent.

In its un-coupled form, m and n in Formula I would both be 1, as shown in Formula II below.

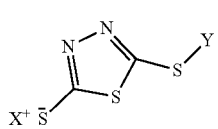

Formula II

The reaction products can also be further reacted with an oxidizing agent, such as, for example, hydrogen peroxide, to form a sulfur coupled "bis-" form of the particular derivative. In the case were the DMTD derivative is sulfur coupled, "n" in Formula I would be 2, "m" could be 1, 2 or 3, and "X" and the positive and negative charges associated therewith would be absent. Such coupled DMTD derivatives can be prepared by preparing the un-coupled compound and then introducing an oxidizing reagent, such as hydrogen peroxide or others, as would be known by those of ordinary skill in the art. Examples of coupled DMTD derivative are shown in Formulas III, IV and V below.

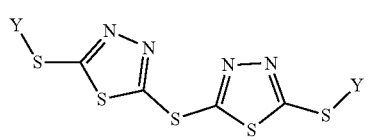

Formula III

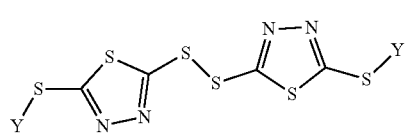

Formula IV

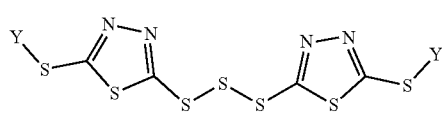

Formula V

In a particular embodiment, the DMTD derivatives can be the reaction product resulting from the displacement using electron deficient hydrocarbons between DMTD and a halogenated ether ("halo-ether") group (which include simple ethers as well as polyethers). The foregoing reaction product can further be reacted in an acid-base reaction with a base to form a salt or an oxidizing agent to form a bis-compound.

As used herein, the term "group," for example as in a halogenated alkyl or aryl group, halo-ether group, halo-alcohol group, (meth)acrylate group, and (meth)acrylamide group, depending on the context, refers to the structure of the stated group on its own or as the structure in which the group would form after reaction with another compound. For example, a methyl group could be $CH_4$, as in its lone state, or —$CH_3$ as in its bonded form, or, as a further example, methyl acrylate, could refer to $CH_2$=$CHC(O)OCH_3$, as in its lone state, or —$CH_2CH_2C(O)OCH_3$, as in its bonded form.

In the DMTD derivatives resulting from the displacement using electron deficient hydrocarbons between DMTD and a halo-ether group, the substituent Y of the DMTD derivatives of Formula I would be "$[RO]_oR$," with R and o as defined above.

The mono-ether DMTD derivatives may be represented by formula VI:

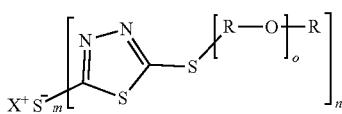

Formula VI where X, R, m, and n are as set forth for Formula I, and "o" is an integer from 1 to 100, or 1 to 75, or 1 to 50, or 1 to 25, or 1 to 20, or 1 to 15, or 1 to 10, or 2 to 10 or 4 to 10 or 6 to 10.

Where the mono-ether DMTD derivative is not reacted with a base, the mono-ether DMTD derivative would be represented by:

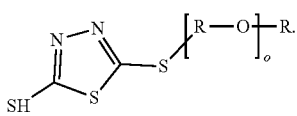

Where the mono-ether DMTD derivative is reacted with a base, the mono-ether DMTD derivative would be represented by:

[Structure]

Where the mono-ether DMTD derivative is reacted with an oxidizing reagent, the mono-ether DMTD derivative would be represented by:

[Structure]

Example simple ethers (i.e., the $[RO]_oR$ group where o is 1) that may be employed include dimethyl ether (both R's are methyl groups, o is 1), diethyl ether (both R's are ethyl groups, o is 1), dipropyl ether (both R's are propyl groups, o is 1), methyl ethyl ether (one R is a methyl group, one R is an ethyl group, o is 1), methyl phenyl ether (one R is a methyl group, one R is n phenyl group, o is 1).

Example polyethers (i.e., the $[RO]_oR$ group where o is 2 to 100) that may be employed include paraformaldehyde (i.e., the $[RO]_oR$ group where the repeating R is a methyl group and the non-repeating R is H, o is 8 to 100), polyethylene glycol (i.e., the $[RO]_oR$ group where the repeating R is an ethyl group and the non-repeating R is H, o is 2 to 100), polypropylene glycol (i.e., the $[RO]_oR$ group where the repeating R is an iso-propyl group and the non-repeating R is H, o is 2 to 100), polytetrahydrofuran (i.e., the $[RO]_oR$ group where the repeating R is a butyl group and the non-repeating R is H, o is 2 to 100).

In an example embodiment, DMTD can be reacted with a halomethyl ether, and optionally a base and/or oxidizing reagent, to provide a mono-ether DMTD derivative of one or more of formula VI(1), (2), (3), or (4).

VI(1)
[Structure]

VI(2)
[Structure]

VI(3)
[Structure]

VI(4)
[Structure]

In a further example embodiment, DMTD can be reacted with a polyethylene glycol halide, and optionally a base and/or oxidizing reagent, to provide a mono-ether DMTD derivative of one or more of formula VI(5), (6), (7), or (8):

VI(5)
[Structure]

VI(6)
[Structure]

VI(7)
[Structure]

VI(8)
[Structure]

Similarly, the DMTD derivatives can be the reaction product resulting from the displacement using electron deficient hydrocarbons between DMTD and a halogenated alcohol ("halo-alcohol") group. Similar DMTD derivatives can be prepared from an epoxide opening reaction between DMTD and an epoxide group. The foregoing reaction products can further be reacted in an acid-base reaction with a base to form a salt, or an oxidizing agent to form a bis-compound.

In the alcohol containing DMTD derivatives resulting either from the displacement using electron deficient hydrocarbons between DMTD and a halo-alcohol, or from an epoxide opening reaction between DMTD and an epoxide group, the substituent Y of the DMTD derivatives of Formula I would be "$R[OH]_pA$," and R, p and A as defined above. The mono-alcohol DMTD derivatives may be represented by formula VII:

Formula VII
[Structure]

where X, R, m, and n are as set forth for Formula I, and "p" is an integer from 1 to 6 and "A" is H or an amine, such as a trialkyl amine or a quaternary amine salt.

Where the mono-alcohol DMTD derivative is not reacted with a base, the mono-alcohol DMTD derivative would be represented by:

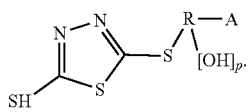

Where the mono-alcohol DMTD derivative is reacted with a base, the mono-alcohol DMTD derivative would be represented by:

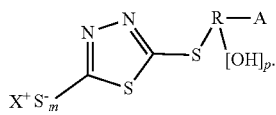

Where the mono-alcohol DMTD derivative is reacted with an oxidizing reagent, the mono-alcohol DMTD derivative would be represented by:

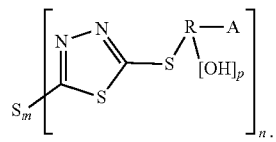

Example mono-alcohols (i.e., the $R[OH]_pA$ group where p is 1 and A is H) include propanol (i.e., R is a linear or branched propyl group) which would be obtained, for example, from a halogenated propanol, such as chloropropanol or propylene oxide; hexanol (i.e., R is a linear or branched hexyl group) which would be obtained, for example, from a halogenated hexanol, such as chlorohexanol; butanol (i.e., R is a linear or branched butyl group) which would be obtained, for example, from a halogenated butanol, such as chlorobutanol or butylene oxide; phenyl propanol (i.e., R is propyl or ethylbenzene) which would be obtained, for example, from a halogenated phenyl propanol group, such as chlorophenylethanol or styrene oxide.

Example polyols (i.e., the $R[OH]_pA$ group where p is 2 to 6 and A is H) that may be employed include sugar alcohols, polyvinyl alcohols, ethylene glycol (i.e., R is an ethyl group, p is 2), propylene glycol (i.e., R is a linear or branched propyl group, p is 2), butanediol (i.e., R is a linear or branched butyl group, p is 2), glycerol (i.e., R is a butyl group, p is 3).

Example alcohol amines (i.e., the $R[OH]_pA$ group where A is an amine) that may be employed include ethanolamine (i.e., R is an ethyl group, p is 1, A is $NH_2$), propanolamine (i.e., R is a propyl group, p is 1, A is $NH_2$), propanol dimethylamine (i.e., R is a propyl group, p is 1, A is $N(CH_3)_2$), propanol quaternary amine halide salt (i.e., R is a propyl group, p is 1, A is a $N^+(CH_3)_3 \cdot Cl^-$).

In an example embodiment, DMTD can be reacted with a glycidol, and optionally a base and/or oxidizing reagent, to provide a mono-alcohol derivative of one or more of formula VII(1), (2), (3), or (4).

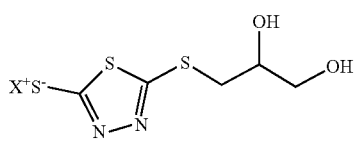

VII(1)

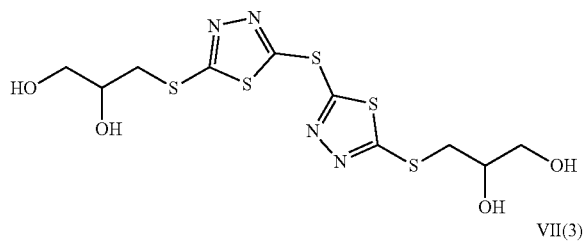

VII(2)

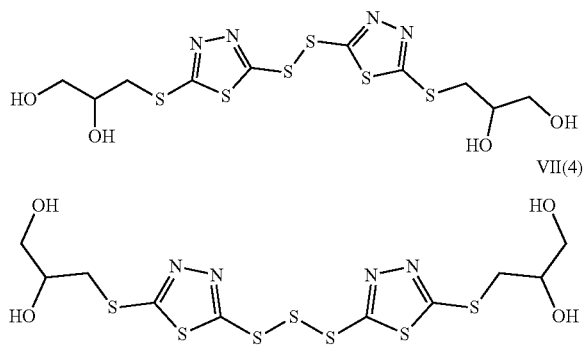

VII(3)

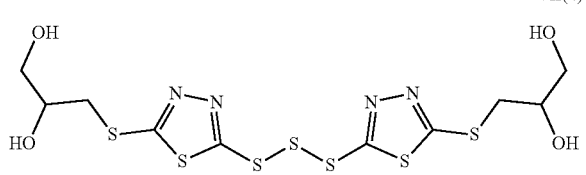

VII(4)

In a further example embodiment, DMTD can be reacted with a glycidol methacrylate, and optionally a base and/or oxidizing reagent, to provide a mono-alcohol derivative of one or more of formula VII(5), (6), (7), or (8).

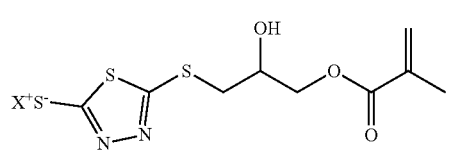

VII(5)

VII(6)
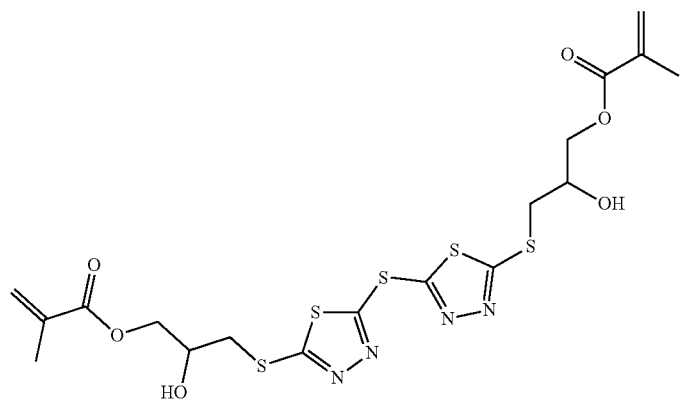
VII(7)
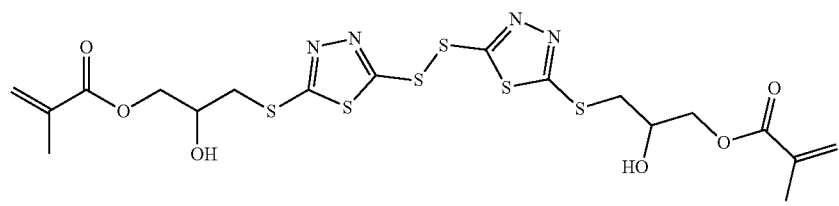
VII(8)
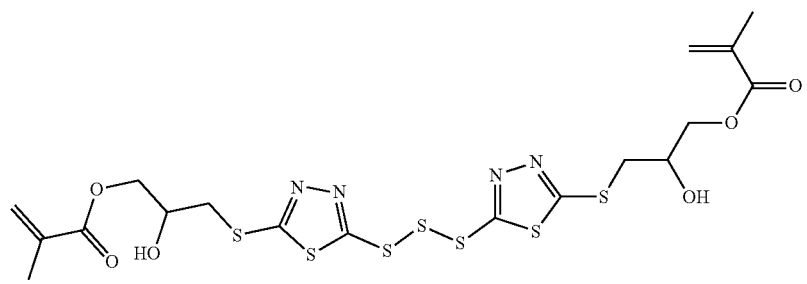
In a still further example embodiment, DMTD can be reacted with a 2-epoxy quaternary ethyl amine halide, and optionally a base and/or oxidizing reagent, to provide a mono-alcohol derivative of one or more of formula VII(9), (10), (11), or (12).
VII(9)
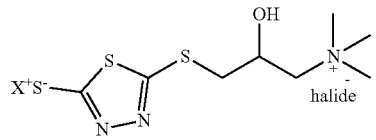
VII(10)
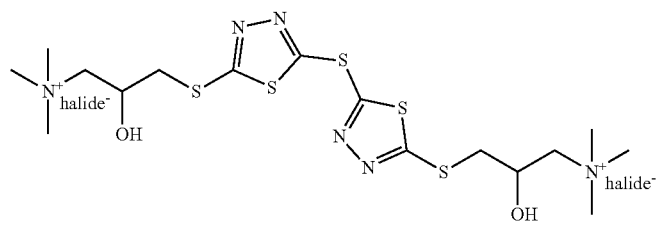

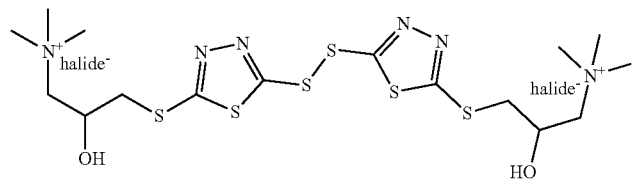

VII(11)

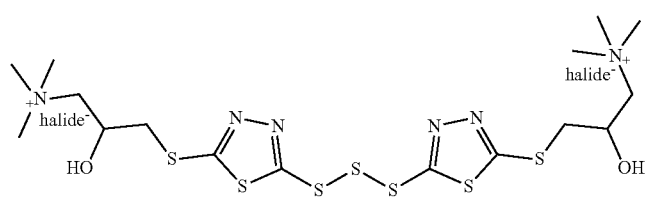

VII(12)

The DMTD derivatives can also be the reaction product resulting from a 1,4 addition between DMTD and a carboxamide group capable of 1,4 addition. The foregoing reaction product can further be reacted in an acid-base reaction with a base to form a salt or an oxidizing agent to form a bis-compound.

Carboxamide groups capable of 1,4 addition can be readily envisaged by those of skill in the art, and include, both mono-carboxamides and di-carboxamides. Example carboxamides can include, but not be limited to, itaconic amide, citraconic amide, maleic amide, fumaric amide, mesaconic amide, as well as (meth)acrylamide. The carboxamides can be primary, or can be substituted with one or more "R" groups to form a secondary or tertiary amide group.

As used herein, the parentheses "( )" around the term "meth" means the term "meth" may or may not be present. Thus, (meth)acrylate can refer to both acrylate and methacrylate, and (meth)acrylamide includes both acrylamide and methacrylamide.

In a particular example, carboxamide containing DMTD derivatives can result from 1,4 addition between DMTD and a (meth)acrylamide group, wherein the substituent Y of the DMTD derivatives of Formula I would be "CH$_2$CH[CH$_3$ or H]C(O)NHZ," and Z is as defined above. Such mono-(meth)acrylamide DMTD derivatives may be represented by formula VIII:

Formula VIII

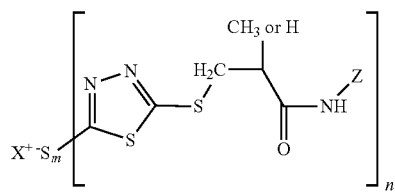

where X, m, and n are as set forth for Formula I, and "Z" is H, "R," RSO$_3^-$Na$^+$, RSO$_3$H, or RN$^+$(R)$_3$Cl$^-$.

Where the mono-(meth)acrylamide DMTD derivative is not reacted with a base, the mono-ether DMTD derivative would be represented by:

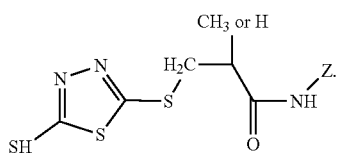

Where the mono-(meth)acrylamide DMTD derivative is reacted with a base, the mono-ether DMTD derivative would be represented by:

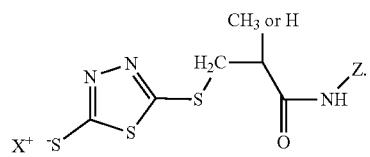

Where the mono-(meth)acrylamide DMTD derivative is reacted with an oxidizing reagent, the mono-ether DMTD derivative would be represented by:

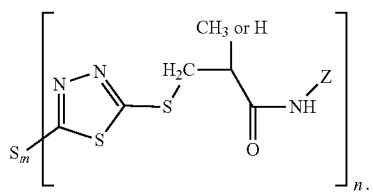

In some embodiments, DMTD can be reacted with methacrylaminopropyl trimethyl ammonium chloride to provide a mono-methacrylamide DMTD derivative of Formula VIII, in either coupled or un-coupled form, where Z (CH$_2$)$_3$N$^+$(CH$_3$)$_3$Cl$^-$, m is 1, 2 or 3 and n is 1 or 2 and X is an optional alkali or alkaline earth metal or amine.

In some embodiments, DMTD can be reacted with 2-acrylamino-2-methylpropane sulfonic acid to provide a DMTD derivative of Formula VIII, in either coupled or un-coupled form, where Z is C(CH$_3$)$_2$CH$_2$SO$_3$H, m is 1, 2 or 3 and n is 1 or 2 and X is an optional alkali or alkaline earth metal or amine.

In some embodiments, DMTD can be reacted with 2-acrylamino-2-methylpropane sulfonic acid sodium salt to provide a DMTD derivative of Formula VIII, in either coupled or un-coupled form, where Z is C(CH$_3$)$_2$CH$_2$SO$_3^-$ Na$^+$, m is 1, 2 or 3 and n is 1 or 2 and X is an optional alkali or alkaline earth metal or amine.

Likewise, the DMTD derivatives can also be the reaction product resulting from a 1,4 addition between DMTD and a carboxylate group capable of 1,4 addition. The foregoing reaction product can further be reacted in an acid-base reaction with a base to form a salt or an oxidizing agent to form a bis-compound.

Carboxylate groups capable of 1,4 addition can be readily envisaged by those of skill in the art, and include, both mono-carboxylates and di-carboxylates as well as higher carboxylates, e.g., tricarboxylates, tetracarboxylates, etc. Example carboxylates can include, but not be limited to, itaconates, citraconates, maleates, fumarates, mesaconates, as well as (meth)acrylates. The carboxylates can be in the form of a salt with an alkali or alkaline earth metal, an ammonia group, or an ester with an "R" group. Where the salt is desired, it can be obtained by 1,4 addition of the salted monomer, or by addition of the ester followed by saponification with an alkali or alkaline earth metal hydroxide or ammonium hydroxide. In some embodiments, the carboxylate does not include a (meth)acrylic acid or a (meth)acrylate where the ester group of the (meth)acrylate is a simple R group.

In general, the carboxylate containing DMTD derivatives can result from 1,4 addition between DMTD and a carboxylic acid or carboxylate. Where the 1,4 addition is with a carboxylic acid, the reaction will be followed by reaction with the desired base to form the salt. For example, DMTD may be reacted with aconitic acid to form a DMTD derivative with an aconitic acid connected off of a substituent sulfur, followed by reaction with an alkali metal hydroxide, alkali earth metal hydroxide, or ammonium hydroxide. Such a reaction could be represented, for example, by the following reaction mechanism:

A further example could be a carboxylate containing DMTD derivative resulting from the 1,4 addition between DMTD and a dialkyl itaconate, such as dimethyl itaconate, wherein the substituent Y of the DMTD derivatives of Formula I would be dimethyl itaconate, for example, as represented by formula

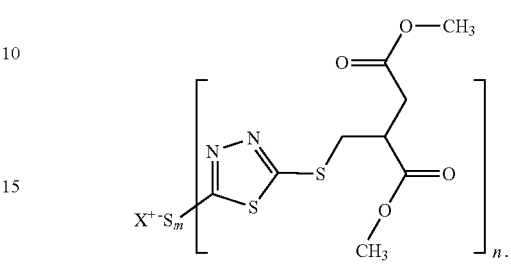

In the foregoing example, the carboxylate could also be, for example, a dialkali or dialkaline earth itaconate salt, such disodium itaconate, represented, for example, by formula

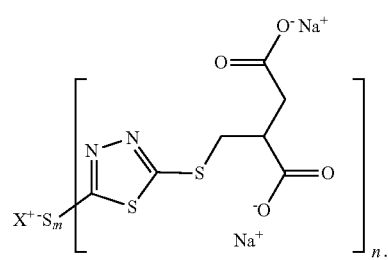

Another example carboxylate containing DMTD derivative can result from 1,4 addition between DMTD and a

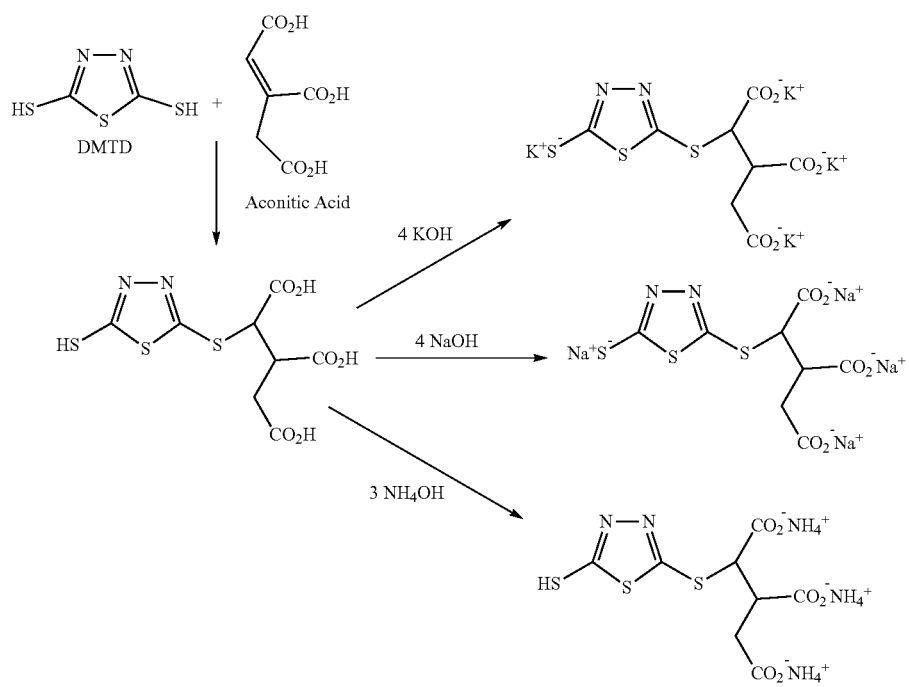

dialkyl maleate, such as dimethyl maleate, wherein the substituent Y of the DMTD derivatives of Formula I would be dimethyl maleate, for example, as represented by formula

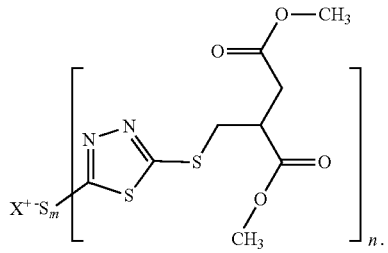

In the foregoing example, the carboxylate could also be, for example, a dialkali or dialkaline earth maleate salt, such disodium maleate, represented, for example, by formula

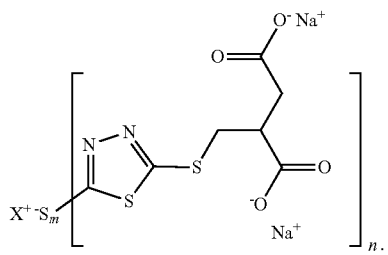

Further examples can include, for example, the reaction of methyl acrylate and DMTD, or dimethyl maleate and DMTD. Where the salts are desired, these examples can also include, for example, the reaction of sodium acrylate or disodium maleate, or the foregoing esters could be saponified in the presence of sodium hydroxide to obtain the salts.

In further examples, a carboxylate containing DMTD derivatives can result from 1,4 addition between DMTD and a (meth)acrylate group in which the ester group is a quaternary ammonium group or a sulfur trioxide containing group, wherein the substituent Y of the DMTD derivatives of Formula I would be "CH$_2$CH[CH$_3$ or H]C(O)OZ." The mono-(meth)acrylate DMTD derivatives may be represented by formula IX:

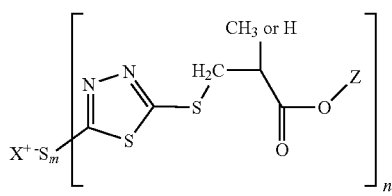

Formula IX where X, m, and n are as set forth for Formula I, and "Z" is X, RSO$_3^-$Na$^+$, RSO$_3$H, RN$^+$(R)$_3$SO$_3^-$, RN$^+$(R)$_3$SO$_3^-$K$^+$, RSO$_3^-$NH$_4^+$ or RN$^+$(R)$_3$Cl$^-$.

Where the mono-(meth)acrylate DMTD derivative is not reacted with a base, the mono-ether DMTD derivative would be represented by:

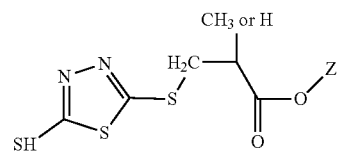

where Z is X, RSO$_3^-$Na$^+$, RSO$_3$H, RN$^+$(R)$_3$SO$_3^-$, RN$^+$(R)$_3$SO$^-$K$^+$, RSO$_3^-$NH$_4^+$ or RN$^+$(R)$_3$Cl$^-$.

Where the mono-(meth)acrylate DMTD derivative is reacted with a base, the mono-ether DMTD derivative would be represented by:

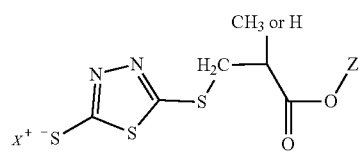

where Z is X, RSO$_3^-$Na$^+$, RSO$_3$H, RN$^+$(R)$_3$SO$_3^-$, RN$^+$(R)$_3$SO$_3^-$K$^+$, RSO$_3^-$NH$_4^+$ or RN$^+$(R)$_3$Cl$^-$.

Where the mono-(meth)acrylate DMTD derivative is reacted with an oxidizing reagent, the mono-ether DMTD derivative would be represented by:

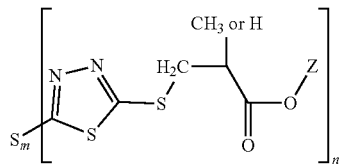

where Z is X, RSO$_3^-$Na$^+$, RSO$_3$H, RN$^+$(R)$_3$SO$_3^-$, RN$^+$(R)$_3$SO$_3^-$1K$^+$, RSO$_3^-$NH$_4^+$ or RN$^+$(R)$_3$Cl$^-$.

In an example embodiment, DMTD can be reacted with methacryloxyethyl trimethyl ammonium chloride to provide a mono-methacrylate DMTD derivative of Formula IX, in either coupled or un-coupled form, where Z is (CH$_2$)$_2$N$^+$(CH$_3$)$_3$Cl$^-$, m is 1, 2 or 3 and n is 1 or 2 and X is an optional alkali or alkaline earth metal or amine.

Likewise, the DMTD derivatives can also be the reaction product resulting from a 1,4 addition between DMTD and a (meth)acrylate group and an oxidizing agent to form a bis-compound.

In bis-(meth)acrylate containing DMTD derivatives resulting from 1,4 addition between DMTD and a (meth)acrylate group and an oxidizing agent, the substituent Y of the DMTD derivatives of Formula I would be "CH$_2$CH[CH$_3$ or H]C(O)OZ," and Z is R or H. The mono-(meth)acrylate DMTD derivatives may be represented by formula X:

Formula X

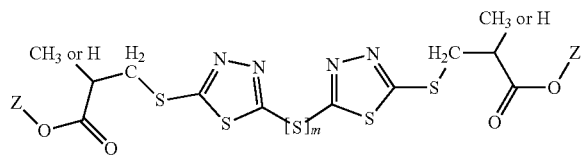

where m is 1, 2 or 3 and "Z" is R or H.

In an example embodiment, DMTD can be reacted with methyl acrylate, followed by an oxidizing agent to provide mono-acrylate bis-DMTD derivative of Formula X, where Z is CH₃, and m is 1, 2 or 3.

In another example embodiment, DMTD can be reacted with 2-ethylhexyl acrylate, followed by an oxidizing agent, to provide a mono-acrylate bis-DMTD derivative of Formula X where Z is a 2-ethylhexyl group, and m is 1, 2 or 3.

The DMTD derivatives can also be the reaction product resulting from the displacement using electron deficient hydrocarbons between DMTD and a halogenated hydrocarbyl ("halo-hydrocarbyl") group (which include linear, branched, saturated or unsaturated, or cyclic alkyl group, or aryl group, where an unsaturated alkyl group is synonymous with an alkene), and further reacted with an oxidizing agent to form a bis-compound.

In the DMTD derivatives resulting from the displacement using electron deficient hydrocarbons between DMTD and a halo-hydrocarbyl group, the substituent Y of the DMTD derivatives of Formula I would be "R," as defined above, n would be 2 and m would be 1, 2 or 3. Although the substituent may be any hydrocarbyl group, the derivative is collectively referred to herein and in the claims as a "mono-alkylated" DMTD derivative.

The mono-alkylated bis-DMTD derivatives may be represented by formulas XI:

Formula XI

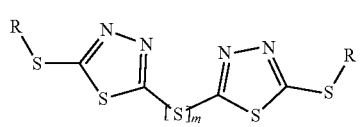

where m is 1, 2 or 3, and R is a linear, branched, saturated or unsaturated, cyclic $C_1$ to $C_{12}$, or $C_1$ to $C_{10}$, or $C_1$ to $C_8$, or even $C_1$ to $C_6$ alkyl or aryl group; or H.

In an example embodiment, DMTD can be reacted with a benzylhalide and an oxidizing reagent, to provide a mono-arylated DMTD derivative of one or more of formula XI(1), (2), or (3).

XI(1)

XI(2)

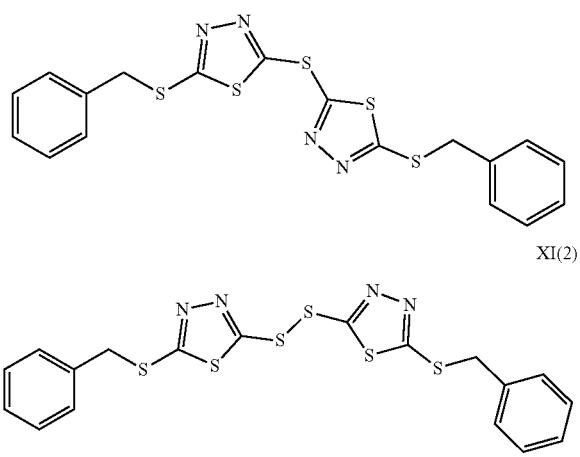

XI(3)

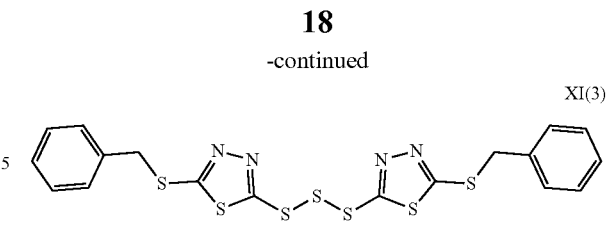

In some embodiments, DMTD derivatives such as those discussed above may include a quaternary ammonium substituent and be treated with a strong base, such as LiOH, NaOH, KOH, Ca(OH)₂, a quaternary amine such as R₄NOH, and the like to produce a zwitterionic species.

The foregoing reaction products can include a zwitterionic mono-quaternary ammonium containing alkyl DMTD derivative represented as shown in formula XII:

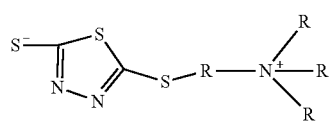

The foregoing reaction products can include a zwitterionic mono-quaternary ammonium containing ether DMTD derivative represented as shown in formula XIII:

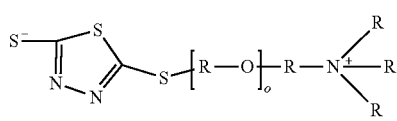

The foregoing reaction products can also include a zwitterionic mono-quaternary ammonium containing alcohol DMTD derivative represented as shown in formula XIV:

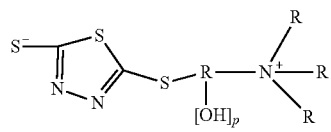

The foregoing reaction products can include a zwitterionic mono-quaternary ammonium containing carboxamide, such as, for example, a (meth)acrylamide DMTD derivative represented as shown in formula XV:

Formula XV

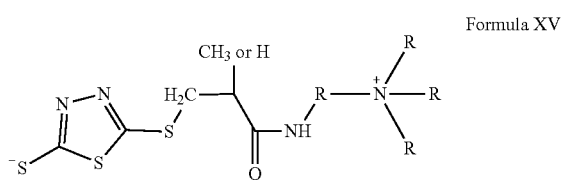

The foregoing reaction products can include a zwitterionic mono-quaternary ammonium containing carboxylate, such as, for example, a (meth)acrylate DMTD derivative represented as shown in formula XVI:

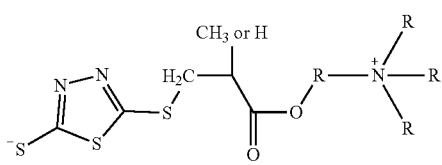

For example, DMTD can be reacted with methacrylaminopropyl trimethyl ammonium chloride to provide a monomethacrylamide DMTD derivative of Formula XV where Z $(CH_2)_3N^+(CH_3)_3Cl^-$, m is 1, 2 or 3 and n is 1 or 2, followed by treatment with NaOH to afford a zwitterion of formula XV':

Formula XV'

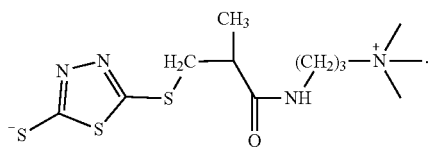

The amount of each chemical component described is presented exclusive of any solvent or diluent oil, which may be customarily present in the commercial material, that is, on an active chemical basis, unless otherwise indicated. However, unless otherwise indicated, each chemical or composition referred to herein should be interpreted as being a commercial grade material which may contain the isomers, by-products, derivatives, and other such materials which are normally understood to be present in the commercial grade.

EXAMPLES

Example 1. Synthesis of 2-(2-Hydroxyethylcarboxyethyl)thio-5-thiol-1,3,4-Thiadiazole. 150.2 grams of DMTD, 150 grams of toluene solvent, and 120 grams of 97% pure 2-hydroxyethyl acrylate were added to a 1-liter flask and heated at 85° C. for five hours. Toluene solvent was vacuum stripped on a rotary evaporator at 3 mm Hg vacuum and 80° C. for four hours. The product was obtained as a viscous yellow liquid after filtration through silicon dioxide filter aid.

Example 2. Synthesis of 2-(2-Ethoxyethoxycarboxyethyl)thio-5-thiol-1,3,4-Thiadiazole 150.2 grams of DMTD, 150 grams of toluene solvent, and 188.2 grams of 2-ethoxyethoxy acrylate were added to a 1-liter flask and heated at 85° C. for two hours. Toluene solvent was vacuum stripped on a rotary evaporator at 3 mm Hg vacuum and 80° C. for four hours. The product was obtained as a viscous yellow liquid.

Example 3. Synthesis of 2-(Methacryloylaminopropyltrimethylammonium chloride)thio-5-thiol-1,3,4-Thiadiazole. 84.1 grams of DMTD, 247 grams of 50% aqueous Methacryloylaminopropyltrimethylammonium chloride, 0.42 gram of sodium hydroxide, and 300 grams of water were added to a one liter flask and heated under nitrogen at 90° C. for 8 hours. The mixture was transferred to an open beaker and most of the water solvent was evaporated in a 65° C. oven on standing, followed by vacuum drying at 2 mm Hg and 95° C. for 20 hours. The final product was a crystalline solid.

Example 4. Synthesis of 2-(Methacryloylaminopropyltrimethylammonium)thio-5-thiolate-1,3,4-Thiadiazole. 122.7 grams of 2-(Methacryloylaminopropyltrimethylammonium chloride) thio-5-thiol-1,3,4-Thiadiazole, 13.2 grams of sodium hydroxide, and 200 grams of deionized water were added to a one liter flask and heated under nitrogen at 70° C. for three hours. The mixture was transferred to an open beaker and most of the water solvent was evaporated in a 65° C. oven on standing, followed by vacuum drying at 5 mm Hg and 95° C. for 18 hours. The crystalline solid obtained was dissolved in 250 mL of ethanol and cooled to precipitate sodium chloride, which was removed by filtration. Ethanol was removed in a 65° C. oven and a vacuum oven to constant weight at 95° C.

Example 5. Synthesis of 2-(Acryloylamino-2-methylpropylsulfonic acid)thio-5-thiol-1,3,4-thiadiazole. 98.15 grams of DMTD, 135.4 grams of 2-Acrylamido-2-methylpropanesulfonic acid, 0.2 gram of sodium hydroxide, and 200 grams of isopropanol solvent were added to a one liter flask and heated under nitrogen at 80° C. for 8 hours. The mixture was transferred to an open beaker and most of the water solvent was evaporated in a 65° C. oven on standing, followed by vacuum drying at 4 mm Hg and 95° C. for 22 hours. The final product was a crystalline solid.

Example 6. Synthesis of Sodium 2-(Acryloylamino-2-methylpropylsulfonate)thio-5-thiol-1,3,4-thiadiazole. 150.2 grams of DMTD, 320.9 grams of 50% aqueous 2-Acrylamido-2-methylpropanesulfonic acid sodium salt, 80 grams of deionized water solvent were added to a one liter flask and heated under nitrogen at 80° C. for 6 hours. The mixture was transferred to an open beaker and most of the water solvent was evaporated in a 65° C. oven on standing, followed by vacuum drying at 3 mm Hg and 100° C. for 16 hours. The final product was a crystalline solid.

Example 7. Synthesis of Disodium 2-(Acryloylamino-2-methylpropylsulfonate)thio-5-thiolate-1,3,4-thiadiazole. 72.7 grams of 2-(Acryloylamino-2-methylpropylsulfonic acid)-5-thiol-1,3,4-thiadiazole prepared in Example 16, 16.25 grams of sodium hydroxide, 200 grams of deionized water solvent were added to a one liter flask and heated under nitrogen at 85° C. for 3 hours. The mixture was transferred to an open beaker and most of the water solvent was evaporated in a 65° C. oven on standing, followed by vacuum drying at 3 mm Hg and 105° C. for 16 hours. The final product was a crystalline solid.

Example 8. Synthesis of 2-(Methacryloyloxyethyl trimethylammonium chloride)thio-5-thiol-1,3,4-Thiadiazole. 65.9 grams of DMTD, 126.5 grams of 72% aqueous Methacryloyloxyethyltrimethylammonium chloride, 0.2 gram of sodium hydroxide, and 125 grams of water were added to a one liter flask and heated under nitrogen at 90° C. for 8 hours. The mixture was transferred to an open beaker and most of the water solvent was evaporated in a 65° C. oven on standing, followed by vacuum drying at 2.5 mm Hg and 95° C. for 23 hours. The final product was a crystalline solid.

Example 9. Synthesis of 2-(2-hydroxypropyltrimethylammonium chloride)thio-5-thiol-1,3,4-thiadiazole. 45.07 grams of DMTD, 45.9 grams of technical grade glycidyltrimethylammonium chloride, and 200 grams of reagent grade acetonitrile solvent were added to a one liter flask and heated under nitrogen at 80° C. for 8 hours. The mixture was transferred to an open beaker and most of the solvent was evaporated in a 65° C. oven on standing, followed by vacuum drying at 3.5 mm Hg and 90° C. for 22 hours. The final product was a yellow crystalline solid.

Example 10. Synthesis of bis-2-(n-Hexyl-5-disulfide)-1,3,4-thiadiazole. 229 grams of 2-(n-Hexyl)thio-5-thiol-1,3,4-Thiadiazole prepared in Example 24 was added to a one liter flask and 55.4 grams of 35% hydrogen peroxide in water was added over 45 minutes while keeping the temperature in the range of 75-80° C. under nitrogen. The reaction was heated at 85° C. for four hours, cooled, and dissolved into 300 mL of reagent grade toluene. This solution was washed with additional deionized water using a separatory funnel, collected, and dried over anhydrous sodium sulfate. The toluene solvent was removed using a rotary evaporator to obtain the disulfide as a low melting wax.

Example 11. Synthesis of Sodium 2-(n-Hexyl)thio-5-thiolate-1,3,4-Thiadiazole. 42.5 grams of 2-(n-Hexyl)thio-5-thiol-1,3,4-Thiadiazole prepared in Example 24, 7.25 grams of sodium hydroxide, and 200 mL of toluene solvent were added to a 1-L flask and heated at reflux for 6 hours. Water distillate was collected using a Dean Stark trap. The reaction mixture was transferred to an open beaker and most of the solvent was evaporated in a 65° C. oven on standing, followed by vacuum drying at 2 mm Hg and 90° C. for 18 hours. The final product was a light yellow solid.

Example 12. Synthesis of 2-[(Methacryloyloxy)ethyl-dimethyl-(3-sulfopropyl)ammonium]thio-5-thiol-1,3,4-Thiadiazole. 86.6 grams of [2-(Methacryloyloxy)ethyl]dimethyl-(3-sulfopropyl)ammonium hydroxide, 46.6 grams of DMTD, 0.3 gram of sodium hydroxide, and 250 grams of deionized water were added to a one liter flask and heated under nitrogen at 85° C. for six hours. The mixture was transferred to an open beaker and most of the water solvent was evaporated in a 65° C. oven on standing, followed by vacuum drying at 3 mm Hg and 85° C. for 18 hours. The product was obtained as a glasslike solid.

Example 13. Synthesis of Potassium 2-[(Methacryloyloxy)ethyl-dimethyl-(3-sulfopropyl)ammonium]thio-5-thiolate-1,3,4-Thiadiazole. 59.3 grams of [2-(Methacryl oyloxy)ethyl] dimethyl-(3 -sulfopropyl)ammonium hydroxide, 40 grams of DMTD mono-potassium salt, 0.3 gram of potassium hydroxide, and 200 grams of deionized water were added to a one liter flask and heated under nitrogen at 85° C. for six hours. The mixture was transferred to an open beaker and most of the water solvent was evaporated in a 65° C. oven on standing, followed by vacuum drying at 5 mm Hg and 85° C. for 20 hours. The product was obtained as a yellow solid.

Example 14. Synthesis of Potassium 2-[(Methacryloyloxy-3-sulfopropyl)thio-5-thiol-1,3,4-Thiadiazole. 73.9 grams of 3-sulfopropyl methacrylate potassium salt, 45.07 grams of DMTD, 0.2 gram of sodium hydroxide, and 250 grams of deionized water were added to a one liter flask and heated under nitrogen at 85-90° C. for 12 hours. The mixture was transferred to an open beaker and most of the water solvent was evaporated in a 65° C. oven on standing, followed by vacuum drying at 3 mm Hg and 90° C. for 28 hours. The product was obtained as a yellow solid.

Example 15. Synthesis of Dipotassium 2-[(Methacryloyloxy-3-sulfopropyl)thio-5-thiolate-1,3,4-Thiadiazole. 49.7 grams of 3-sulfopropyl methacrylate potassium salt, 38 grams of DMTD mono-potassium salt, 0.3 gram of potassium hydroxide, and 225 grams of deionized water were added to a one liter flask and heated under nitrogen at 85° C. for six hours. The clear mixture was transferred to an open beaker and most of the water solvent was evaporated in a 65° C. oven on standing, followed by vacuum drying at 3.5 mm Hg and 95° C. for 24 hours. The product was obtained as an amber solid.

Example 16. Synthesis of Dipotassium 2-(2-methylethyl-2-carboxylate)thio-5-thiolate-1,3,4-Thiadiazole. 100 grams of ester prepared in Example 23, 44.8 grams of potassium hydroxide, and 300 grams of deionized water were added to a one liter flask and heated at reflux (90° C.) for 14 hours while collecting distillate in a Dean Stark trap. The clear mixture was transferred to an open beaker and most of the water solvent was evaporated in a 65° C. oven on standing, followed by vacuum drying at 4.5 mm Hg and 95° C. for 26 hours. The product was obtained as a light yellow crystalline solid.

Example 17. Synthesis of Disodium 2-(Propyl-2,3-dicarboxylate)thio-5-thiol-1,3,4-Thiadiazole. 65.25 grams of Itaconic acid, 75.1 grams of DMTD, 0.3 gram of sodium hydroxide, and 200 grams of deionized water were added to a one liter flask and heated under nitrogen at 90° C. for six hours. The clear mixture was cooled to room temperature and 40 grams of sodium hydroxide addded, followed by heating at 70° C. for four hours. The mixture was transferred to an open beaker and most of the water solvent was evaporated in a 65° C. oven on standing, followed by vacuum drying at 4 mm Hg and 95° C. for 26 hours. The product was obtained as a yellow solid powder.

Example 18. Synthesis of Trisodium 2-(Propyl-2,3-dicarboxylate)thio-5-thiolate-1,3,4-Thiadiazole. 40 grams of DMTD mono-sodium salt, 30.2 grams of Itaconic acid, and 250 grams of deionized water were added to a one liter flask. 18.6 grams of sodium hydroxide was then added the mixture heated under nitrogen at 90° C. for 12 hours. The mixture was cooled to room temperature and a small amount of insoluble solid removed through filter paper. The clear mixture was transferred to an open beaker and most of the water solvent was evaporated in a 65° C. oven on standing, followed by vacuum drying at 2 mm Hg and 100° C. for 28 hours. The product was obtained as a yellow solid powder.

Example 19. Synthesis of Disodium 2-(Ethyl-2,3-dicarboxylate)thio-5-thiol-1,3,4-Thiadiazole. 46.45 grams of maleic acid, 60.1 grams of DMTD, 0.25 gram of sodium hydroxide, and 175 grams of deionized water were added to a one liter flask and heated under nitrogen at 90° C. for six hours. The clear mixture was cooled to room temperature and 32 grams of sodium hydroxide addded, followed by heating at 70° C. for four hours. The mixture was transferred to an open beaker and most of the water solvent was evaporated in a 65° C. oven on standing, followed by vacuum drying at 2 mm Hg and 95° C. for 24 hours. The product was obtained as a yellow solid.

Example 20. Synthesis of Disodium 2-(2-methylethyl-2-carboxylate)thio-5-thiolate-1,3,4-Thiadiazole. 35 grams of DMTD mono-sodium salt, 22 grams of sodium methacrylate, 0.3 gram of sodium hydroxide catalyst, and 200 grams of deionized water solvent were added to a one liter flask and heated at 90° C. for 8 hours and cooled. A small amount of an insoluble solid was removed by filtration through filter paper. The clear mixture was transferred to an open beaker and most of the water solvent was evaporated in a 65° C. oven on standing, followed by vacuum drying at 2.5 mm Hg and 95° C. for 24 hours. The product was obtained as a light yellow solid.

Example 21. Synthesis of 2-(2-Ethylhexylcarboxyethyl)thio-5-thiol-1,3,4-Thiadiazole. 150.2 grams of DMTD, 150 grams of toluene solvent, and 184.3 grams of 2-ethylhexyl acrylate were added to a 1-liter flask and heated at 85° C. for 7 hours. Toluene solvent was vacuum stripped on a rotary evaporator at 2 mm Hg vacuum and 80° C. for 5 hours to provide the desired product as a yellow liquid.

Example 22. Synthesis of 2-(Laurylcarboxy-2-methylethyl)thio-5-thiol-1,3,4-Thiadiazole. 129 grams of DMTD, 216.2 grams of lauryl methacrylate, and 0.2 gram of sodium hydroxide catalyst were added to a one liter flask and heated at 105° C. for 14 hours after which time the reaction was clear and all of the starting materials had dissolved. The mixture was vacuum stripped on a rotary evaporator for six hours at 2 mm Hg vacuum and 80° C. to provide the desired product as a low melting solid.

Example 23. Synthesis of 2-(Methylcarboxy-2-methylethyl)thio-5-thiol-1,3,4-Thiadiazole. 182.1 grams of DMTD, 121.3 grams of methyl methacrylate, 0.3 gram of potassium t-butoxide catalyst, and 400 mL of toluene solvent were added to a two liter flask and heated at 100° C. for 12 hours after which time a small amount of a yellow solid was removed by filtration. The mixture was vacuum stripped on a rotary evaporator for six hours at 2 mm Hg vacuum and 80° C. to provide the desired product as a yellow solid upon cooling.

Example 24. Synthesis of 2-(n-Hexyl)thio-5-thiol-1,3,4-Thiadiazole. 150.2 grams of DMTD and 900 mL of ethanol were added to a 3-L flask and 56.1 grams of potassium hydroxide was added in portions over a 30 minute period. The reaction was heated at 75° C. for 2 hours under nitrogen and cooled to 24° C. 165.1 grams of n-hexylbromide was added over 20 minutes and the mixture heated at reflux (77° C.) for 6 hours. Ethanol was distilled from the reaction and the residue dissolved into 400 grams of water/600 mL of toluene and transferred to a separatory funnel. The organic phase was washed with additional water, collected, and dried over anhydrous sodium sulfate. After removal of the toluene on a rotary evaporator, the low-melting solid obtained was recrystallized from reagent grade toluene:n-hexane (80:20) wt.:wt. and dried in a vacuum oven to obtain the pure product.

Examples 25-28. Using a similar procedure as Example 24 from the corresponding alkyl bromides, the following DMTD mono-alkylates were prepared:

Example 25. 2-(2-Ethylhexyl)thio-5-thiol-1,3,4-Thiadiazole

Example 26. 2-Cyclohexylthio-5-thiol-1,3,4-Thiadiazole

Example 27. 2-Isoamylthio-5-thiol-1,3,4-Thiadiazole

Example 28. 2-(Ethylcarboxymethylene)thio-5-thiol-1,3,4-Thiadiazole

Example 29. Synthesis of 2-(2,3-Dicarboxypropyl)thio-5-thiol-1,3,4-Thiadiazole. 105.16 g of 2,5-dimercapto-1,3,4-thiadiazole, 300 g of deionized water, 91.1 g of itaconic acid and 0.3 g of sodium hydroxide catalyst were added to a 1-L flask and heated under nitrogen at 88° C. for 10 hours and cooled. Most of the water was evaporated in a steam oven at 65° C. in an open beaker. The product was then dried in a vac oven at 95° C. until constant weight. The product yield was 194 g.

Examples 30-33. A procedure similar to Example 29 was used starting from acrylic acid, methacrylic acid, maleic acid, or aconitic acid to prepare the following:

Example 30. 2-(2-Carboxyethyl)thio-5-thiol-1,3,4-thiadiazole

Example 31. 2-(2-Methylethyl-2-carboxy)thio-5-thiol-1,3,4-thiadiazole

Example 32. 2-(2,3-Dicarboxyethyl)thio-5-thiol-1,3,4-thiadiazole

Example 33. 2-(1,2,3-Tricarboxypropyl)thio-5-thiol-1,3,4-thiadiazole

Example 34 (Alternate procedure for Example 18) Synthesis of Trisodium 2-(propyl-2,3-dicarboxylate)thio-5-thiolate-1,3,4-thiadiazole. 32 g of the diacid product prepared in Example 29, 250 g of deionized water, and 13.7 g of sodium hydroxide were added to a 1-L flask and heated under nitrogen at 85° C. for 6 hours. The mixture was transferred to an open beaker and most of the water evaporated in a steam oven at 65° C. The product was dried in a vacuum oven at 95° C. to constant weight to obtain 38.8 g of a light yellow solid.

Examples 35-41. The procedure of Example 34 was used to prepare the following products from the corresponding carboxylic acids of Examples 29-33:

Example 35. Dipotassium 2-(ethyl-2-carboxylate)thio-5-thiolate-1,3,4-thiadiazole Example 36. Tripotassium 2-(ethyl-1,2-dicarboxylate)thio-5-thiolate-1,3,4-thiadiazole Example 37. Tripotassium 2-(propyl-2,3-dicarboxylate)thio-5-thiolate-1,3,4-thiadiazole Example 38. (Alternate procedure for Example 16) Dipotassium 2-(2-methylethyl-2-carboxylate)thio-5-thiolate-1,3,4-thiadiazole Example 39. (Alternate procedure for Example 20). Disodium 2-(2-methylethyl-2-carboxylate)thio-5-thiolate-1,3,4-thiadiazole Example 40. Tetrasodium 2-(propyl-1,2,3-tricarboxylate)thio-5-thiolate-1,3,4-thiadiazole Example 41. Tetrapotassium 2-(propyl-1,2,3-tricarboxylate)thio-5-thiolate-1,3,4-thiadiazole Example 42. Synthesis of Diammonium 2-(propyl-2,3-dicarboxylate)thio-5-thiol-1,3,4-thiadiazole. 40 g of the diacid product prepared in Example 29, 19 g of aqueous ammonia solution, and 212.8 of deionized water were added to a 1-L flask and stirred under nitrogen at 25° C. for three hours. The reaction mixture was clear and free of solids. 271 g of a 20% weight product solution in water was obtained.

Example 43. Synthesis of Triammonium 2-(propyl-1,2,3-tricarboxylate)thio-5-thiol-1,3,4-thiadiazole. A procedure similar to Example 42 was used starting from the triacid prepared in Example 33 to prepare this product as a 20.3% weight solution in deionized water.

Each of the documents referred to above is incorporated herein by reference, including any prior applications, whether or not specifically listed above, from which priority is claimed. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about." It is to be understood that the upper and lower amount, range, and ratio limits set forth herein may be independently combined. Similarly, the ranges and amounts for each element of the invention can be used together with ranges or amounts for any of the other elements.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of," where "consisting of" excludes any element or step not specified and "consisting essentially of" permits the inclusion of additional un-recited elements or steps that do not materially affect the essential or basic and novel characteristics of the composition or method under consideration.

While certain representative embodiments and details have been shown for the purpose of illustrating the subject invention, it will be apparent to those skilled in this art that various changes and modifications can be made therein without departing from the scope of the subject invention. In this regard, the scope of the invention is to be limited only by the following claims.

A DMTD derivative comprising, consisting essentially of, consisting of the reaction product of:
a. 2,5-dimercapto-1,3,4-thiadiazole ("DMTD"), and
b. at least one of a:
i. halo-ether group,
ii. a halo-alcohol group,
iii. an epoxide group,
iv. a carboxamide group,
v. a carboxylate group.

The DMTD derivative of any previous paragraph, wherein the reaction product comprises, consists essentially of, consists of a compound of formula I

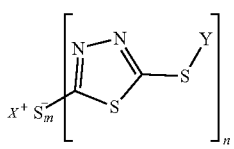

Formula I where
each "X," individually, is an alkali or alkaline earth metal, such as Li, Na, K, Mg, or Ca, a trialkyl amine, or a quaternary amine (including ammonia), or H;
"m" is 1, 2 or 3, and "n" is 1 or 2; and
where "Y" is:
"[RO]$_o$R," where "o" is an integer from 1 to 100;
"R[OH]$_p$A," where "p" is an integer from 1 to 6 and "A" is H or an amine, such as a trialkyl amine or a quaternary amine salt;
a carboxamide, such as a (meth)acrylamide of "CH$_2$CH[CH$_3$ or H]C(O)NHZ,"
where "Z" is H, "R," "RSO$_3^-$Na$^+$," "RSO$_3$H," or "RN$^+$(R)$_3$Cl$^-$," or
a carboxylate, such as an itaconate, maleate, or, for example, a (meth)acrylate of "CH$_2$CH[CH$_3$ or H]C(O)OZ," where "Z" can be X, RN$^+$(R)$_3$SO$_3^-$, RN$^+$(R)$_3$SO$_3^-$K$^+$, "RSO$_3^-$Na$^+$," RSO$_3^-$NH$_4^+$, "RSO$_3$H," or "RN$^+$(R)$_3$Cl$^-$," and
where "R" is a linear, branched, saturated or unsaturated, or cyclic C$_1$ to C$_{12}$, or C$_1$ to C$_{10}$, or C$_1$ to C$_8$, or even C$_1$ to C$_6$ alkyl or aryl group, or H.

The DMTD derivative of any previous paragraph, wherein the "R" group comprises, consists essentially of, consists of, consists essentially of, consists of a methyl group.

The DMTD derivative of any previous paragraph, wherein the "R" group comprises, consists essentially of, consists of, consists essentially of, consists of an ethyl group.

The DMTD derivative of any previous paragraph, wherein the "R" group comprises, consists essentially of, consists of, consists essentially of, consists of a propyl group.

The DMTD derivative of any previous paragraph, wherein the "R" group comprises, consists essentially of, consists of, consists essentially of, consists of a butyl group.

The DMTD derivative of any previous paragraph, wherein the "R" group comprises, consists essentially of, consists of, consists essentially of, consists of a pentyl group.

The DMTD derivative of any previous paragraph, wherein the "R" group comprises, consists essentially of, consists of, consists essentially of, consists of a hexyl group.

The DMTD derivative of any previous paragraph, wherein the "R" group comprises, consists essentially of, consists of, consists essentially of, consists of a heptyl group.

The DMTD derivative of any previous paragraph, wherein the "R" group comprises, consists essentially of, consists of, consists essentially of, consists of an octyl group.

The DMTD derivative of any previous paragraph, wherein the "R" group comprises, consists essentially of, consists of, consists essentially of, consists of a nonyl group.

The DMTD derivative of any previous paragraph, wherein the "R" group comprises, consists essentially of, consists of, consists essentially of, consists of a decyl group.

The DMTD derivative of any previous paragraph, wherein the "R" group comprises, consists essentially of, consists of, consists essentially of, consists of a undecyl group.

The DMTD derivative of any previous paragraph, wherein the "R" group comprises, consists essentially of, consists of, consists essentially of, consists of a dodecyl group.

The DMTD derivative of any previous paragraph, wherein the "R" group comprises, consists essentially of, consists of, consists essentially of, consists of an isobutyl group.

The DMTD derivative of any previous paragraph, wherein the "R" group comprises, consists essentially of, consists of, consists essentially of, consists of an ethylhexyl group.

The DMTD derivative of any previous paragraph, wherein the "R" group comprises, consists essentially of, consists of, consists essentially of, consists of an isoamyl group.

The DMTD derivative of any previous paragraph, wherein the "R" group comprises, consists essentially of, consists of, consists essentially of, consists of a benzyl group.

The DMTD derivative of any previous paragraph, wherein the "R" group comprises, consists essentially of, consists of, consists essentially of, consists of a cyclohexyl group.

The DMTD derivative of any previous paragraph, wherein "X" comprises, consists essentially of, consists of, consists of, consists essentially of H.

The DMTD derivative of any previous paragraph, wherein the reaction product further comprises, consists essentially of, consists of reaction with a base.

The DMTD derivative of any previous paragraph, wherein "X" comprises, consists essentially of, consists of, consists of, consists essentially of an alkali or alkaline earth metal, a trialkyl amine, a quaternary amine, or combinations thereof.

The DMTD derivative of any previous paragraph, wherein the base comprises, consists essentially of, consists of, consists essentially of, or consists of Li.

The DMTD derivative of any previous paragraph, wherein the base comprises, consists essentially of, consists of, consists essentially of, or consists of Na.

The DMTD derivative of any previous paragraph, wherein the base comprises, consists essentially of, consists of, consists essentially of, or consists of K.

The DMTD derivative of any previous paragraph, wherein the base comprises, consists essentially of, consists of, consists essentially of, or consists of Mg.

The DMTD derivative of any previous paragraph, wherein the base comprises, consists essentially of, consists of, consists essentially of, or consists of Ca.

The DMTD derivative of any previous paragraph, wherein the reaction product further comprises, consists essentially of, consists of reaction with an oxidizing reagent.

The DMTD derivative of any previous paragraph, wherein the reaction product further comprises, consists essentially of, consists of reaction with hydrogen peroxide.

The DMTD derivative of any previous paragraph, wherein the sub stituent Y of the DMTD derivative of formula I is "[RO]$_o$R," where "o" is an integer from 1 to 100.

The DMTD derivative of any previous paragraph, wherein the ether (i.e., "[RO]$_o$R,") of the halogenated ether comprises, consists essentially of, consists of, consists essentially of, consists of dimethyl ether.

The DMTD derivative of any previous paragraph, wherein the ether of the halogenated ether comprises, consists essentially of, consists of, consists essentially of, consists of diethyl ether.

The DMTD derivative of any previous paragraph, wherein the ether of the halogenated ether comprises, consists essentially of, consists of, consists essentially of, consists of dipropyl ether.

The DMTD derivative of any previous paragraph, wherein the ether of the halogenated ether comprises, consists essentially of, consists of, consists essentially of, consists of methyl ethyl ether.

The DMTD derivative of any previous paragraph, wherein the ether of the halogenated ether comprises, consists essentially of, consists of, consists essentially of, consists of methyl phenyl ether.

The DMTD derivative of any previous paragraph, wherein the ether of the halogenated ether comprises, consists essentially of, consists of, consists essentially of, consists of paraformaldehyde.

The DMTD derivative of any previous paragraph, wherein the ether of the halogenated ether comprises, consists essentially of, consists of, consists essentially of, consists of polyethylene glycol.

The DMTD derivative of any previous paragraph, wherein the ether of the halogenated ether comprises, consists essentially of, consists of, consists essentially of, consists of polypropylene glycol.

The DMTD derivative of any previous paragraph, wherein the ether of the halogenated ether comprises, consists essentially of, consists of, consists essentially of, consists of polytetrahydrofuran.

The DMTD derivative of any previous paragraph, wherein the reaction product comprises, consists essentially of, consists of a compound of formula

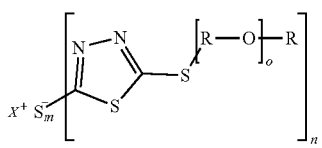

where R, X, o, m and n are as set forth for formula I.

The DMTD derivative of any previous paragraph, wherein the reaction product comprises, consists essentially of, consists of a compound of formula

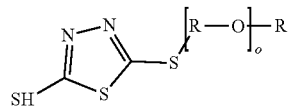

where R and o are as set forth for formula I.

The DMTD derivative of any previous paragraph, wherein the reaction product comprises, consists essentially of, consists of a compound of formula

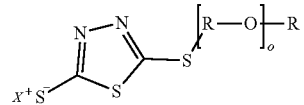

where R, X and o are as set forth for formula I.

The DMTD derivative of any previous paragraph, wherein the reaction product comprises, consists essentially of, consists of a compound of formula

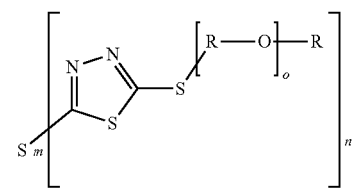

where R, m, n and o are as set forth for formula I.

The DMTD derivative of any previous paragraph, wherein the sub stituent Y of the DMTD derivative of formula I comprises, consists essentially of, consists of "R[OH]$_p$A," where "p" is an integer from 1 to 6 and "A" is H or an amine, such as a trialkyl amine or a quaternary amine salt.

The DMTD derivative of any previous paragraph, wherein the alcohol group (i.e., the R[OH]$_p$A group) comprises, consists essentially of, consists of propanol.

The DMTD derivative of any previous paragraph, wherein the alcohol group (i.e., the R[OH]$_p$A group) comprises, consists essentially of, consists of hexanol.

The DMTD derivative of any previous paragraph, wherein the alcohol group (i.e., the R[OH]$_p$A group) comprises, consists essentially of, consists of butanol.

The DMTD derivative of any previous paragraph, wherein the alcohol group (i.e., the R[OH]$_p$A group) comprises, consists essentially of, consists of phenyl propanol.

The DMTD derivative of any previous paragraph, wherein the alcohol group (i.e., the R[OH]$_p$A group) comprises, consists essentially of, consists of a sugar alcohol.

The DMTD derivative of any previous paragraph, wherein the alcohol group (i.e., the R[OH]$_p$A group) comprises, consists essentially of, consists of a polyvinyl alcohol.

The DMTD derivative of any previous paragraph, wherein the alcohol group (i.e., the R[OH]$_p$A group) comprises, consists essentially of, consists of ethylene glycol.

The DMTD derivative of any previous paragraph, wherein the alcohol group (i.e., the R[OH]$_p$A group) comprises, consists essentially of, consists of propylene glycol.

The DMTD derivative of any previous paragraph, wherein the alcohol group (i.e., the R[OH]$_p$A group) comprises, consists essentially of, consists of butanediol.

The DMTD derivative of any previous paragraph, wherein the alcohol group (i.e., the R[OH]$_p$A group) comprises, consists essentially of, consists of glycerol.

The DMTD derivative of any previous paragraph, wherein the alcohol group (i.e., the R[OH]$_p$A group) comprises, consists essentially of, consists of ethanolamine.

The DMTD derivative of any previous paragraph, wherein the alcohol group (i.e., the R[OH]$_p$A group) comprises, consists essentially of, consists of propanol amine.

The DMTD derivative of any previous paragraph, wherein the alcohol group (i.e., the R[OH]$_p$A group) comprises, consists essentially of, consists of propanol dimethylamine.

The DMTD derivative of any previous paragraph, wherein the alcohol group (i.e., the R[OH]$_p$A group) comprises, consists essentially of, consists of a propanol quaternary amine halide salt.

The DMTD derivative of any previous paragraph, wherein the reaction product comprises, consists essentially of, consists of a compound of formula

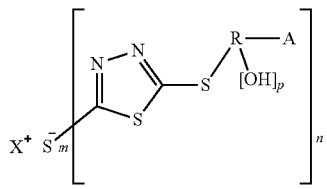

where X, m, n, p, and A are as set forth for formula I.

The DMTD derivative of any previous paragraph, wherein the reaction product comprises, consists essentially of, consists of a compound of formula

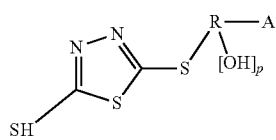

where p and A are as set forth for formula I.

The DMTD derivative of any previous paragraph, wherein the reaction product comprises, consists essentially of, consists of a compound of formula

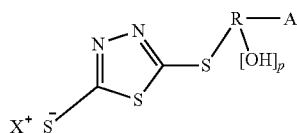

where X, p and A are as set forth for formula I.

The DMTD derivative of any previous paragraph, wherein the reaction product comprises, consists essentially of, consists of a compound of formula

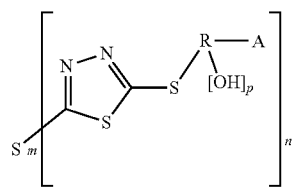

where m, n, p, and A are as set forth for formula I.

The DMTD derivative of any previous paragraph, wherein the DMTD derivative comprises, consists essentially of, consists of the reaction product of DMTD and a carboxamide group.

The DMTD derivative of any previous paragraph, wherein the substituent Y of the DMTD derivative of formula I comprises, consists essentially of, consists of a carboxamide group.

The DMTD derivative of any previous paragraph, wherein the sub stituent Y of the DMTD derivative of formula I comprises, consists essentially of, consists of a mono-carboxamide group.

The DMTD derivative of any previous paragraph, wherein the sub stituent Y of the DMTD derivative of formula I comprises, consists essentially of, consists of a di-carboxamide group.

The DMTD derivative of any previous paragraph, wherein the sub stituent Y of the DMTD derivative of formula I comprises, consists essentially of, consists of a primary carboxamide group.

The DMTD derivative of any previous paragraph, wherein the sub stituent Y of the DMTD derivative of formula I comprises, consists essentially of, consists of a secondary carboxamide group.

The DMTD derivative of any previous paragraph, wherein the sub stituent Y of the DMTD derivative of formula I comprises, consists essentially of, consists of a tertiary carboxamide group.

The DMTD derivative of any previous paragraph, wherein the sub stituent Y of the DMTD derivative of formula I comprises, consists essentially of, consists of an itaconic amide group.

The DMTD derivative of any previous paragraph, wherein the sub stituent Y of the DMTD derivative of formula I comprises, consists essentially of, consists of a maleic amide group.

The DMTD derivative of any previous paragraph, wherein the substituent Y of the DMTD derivative of formula I comprises, consists essentially of, consists of a citraconic amide group.

The DMTD derivative of any previous paragraph, wherein the substituent Y of the DMTD derivative of formula I comprises, consists essentially of, consists of a fumaric amide group.

The DMTD derivative of any previous paragraph, wherein the substituent Y of the DMTD derivative of formula I comprises, consists essentially of, consists of a mesaconic amide group.

The DMTD derivative of any previous paragraph, wherein the substituent Y of the DMTD derivative of formula I comprises, consists essentially of, consists of a (meth)acrylamide group.

The DMTD derivative of any previous paragraph, wherein the substituent Y of the DMTD derivative of formula I comprises, consists essentially of, consists of "CH₂CH[CH₃ or H]C(O)NHZ," where "Z" can be H, "R," "RSO₃⁻Na⁺," "RSO₃H," or "RN⁺(R)₃Cl⁻."

The DMTD derivative of any previous paragraph, wherein the reaction product comprises, consists essentially of, consists of a compound of formula IX

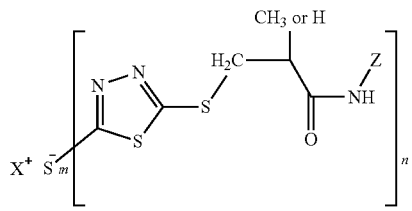

where X, m, n and Z are as set forth for formula I.

The DMTD derivative of any previous paragraph, wherein the reaction product comprises, consists essentially of, consists of a compound of formula IX

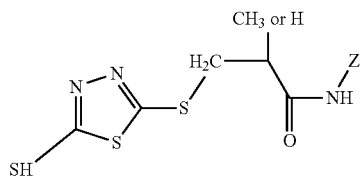

where Z is as set forth for formula I.

The DMTD derivative of any previous paragraph, wherein the reaction product comprises, consists essentially of, consists of a compound of formula IX

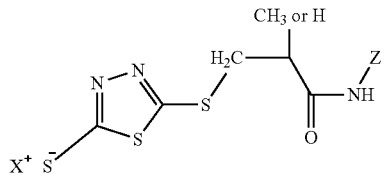

where X and Z are as set forth for formula I.

The DMTD derivative of any previous paragraph, wherein the reaction product comprises, consists essentially of, consists of a compound of formula IX

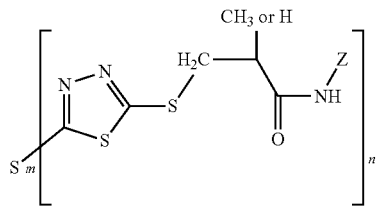

where m, n and Z are as set forth for formula I.

The DMTD derivative of any previous paragraph, wherein the carboxylate comprises, consists essentially of, consists of a di-carboxylate.

The DMTD derivative of any previous paragraph, wherein the carboxylate comprises, consists essentially of, consists of a tri-carboxylate.

The DMTD derivative of paragraph 1, wherein the carboxylate is selected from itaconate, citraconate, maleate, fumarate, mesaconate, where the carboxylates can be in the form of a salt with an alkali or alkaline earth metal, or an ester with an "R" group.

The DMTD derivative of any previous paragraph, wherein the carboxylate does not comprise a (meth)acrylate wherein the ester group of the (meth)acrylate comprises, consists essentially of, consists of H or an R group.

The DMTD derivative of any previous paragraph, wherein the substituent Y of the DMTD derivative of formula I comprises, consists essentially of, consists of "CH₂CH[CH₃ or H]C(O)OZ," where "Z" can be X, RN⁺(R)₃SO₃⁻, RN⁺(R)₃SO₃⁻K⁺, "RSO₃⁻Na⁺," RSO₃⁻NH₄⁺, "RSO₃H," or "RN⁺(R)₃Cl⁻."

The DMTD derivative of any previous paragraph, wherein the reaction product comprises, consists essentially of, consists of a compound of formula

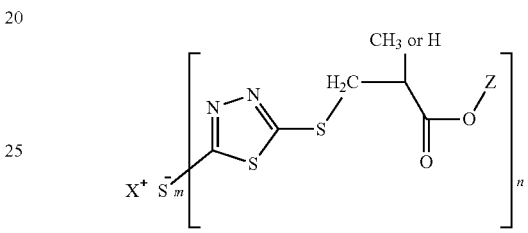

where Z is X, RN⁺(R)₃Cl⁻, RN⁺(R)₃SO₃⁻, RN⁺(R)₃SO₃⁻K⁺, RSO₃⁻Na⁺, RSO₃⁻NH₄⁺, or RSO₃H.

The DMTD derivative of any previous paragraph, wherein the reaction product comprises, consists essentially of, consists of a compound of formula

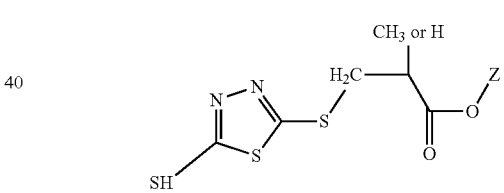

where Z is RN⁺(R)₃Cl⁻, RSO₃⁻Na⁺, or RSO₃H.

The DMTD derivative of any previous paragraph, wherein the reaction product comprises, consists essentially of, consists of a compound of formula

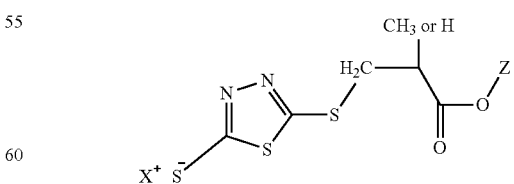

where Z is RN⁺(R)₃Cl⁻, RSO₃⁻Na⁺, or RSO₃H.

The DMTD derivative of any previous paragraph, wherein the reaction product comprises, consists essentially of, consists of a compound of formula

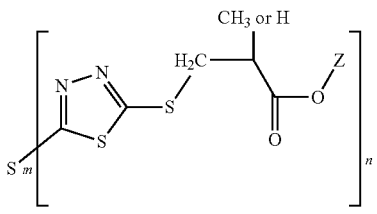

where Z is $RN^+(R)_3Cl^-$, $RSO_3^-Na^+$, or $RSO_3H$.

A zwitterionic DMTD derivative comprising, consisting essentially of, consisting of the reaction product of:
a. 2,5-dimercapto-1,3,4-thiadiazole ("DMTD"), and
b. at least one of
i. a linear, branched, saturated or unsaturated, cyclic halogenated $C_1$ to $C_{22}$ alkyl or aryl quaternary ammonium group,
ii. a quaternary ammonium containing halo-ether group,
iii. a quaternary ammonium containing halo-alcohol group,
iv. a quaternary ammonium containing epoxide group,
v. a quaternary ammonium containing carboxylate group, and
vi. a quaternary ammonium containing carboxamide group, and
c. a strong base.

The zwitterionic DMTD derivative of any previous paragraph wherein the reaction product comprises, consists essentially of, consists of a compound of formula

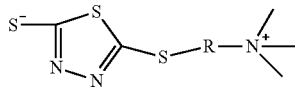

where R is as set forth in any previous paragraph.

The zwitterionic DMTD derivative of any previous paragraph wherein the reaction product comprises, consists essentially of, consists of a compound of formula

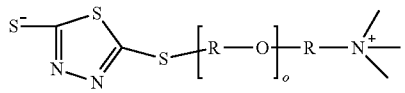

where R and o are as set forth in any previous paragraph.

The zwitterionic DMTD derivative of any previous paragraph wherein the reaction product comprises, consists essentially of, consists of a compound of formula

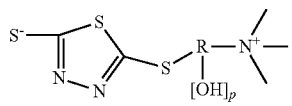

where R and p are as set forth in any previous paragraph.

The zwitterionic DMTD derivative of any previous paragraph wherein the reaction product comprises, consists essentially of, consists of a compound of formula

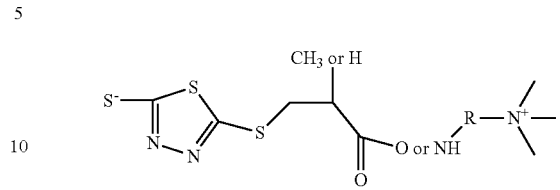

where R is as set forth in any previous paragraph.

A bis-DMTD derivative comprising, consisting essentially of, consisting of the reaction product of
a. 2,5-dimercapto-1,3,4-thiadiazole ("DMTD"), and
b. at least one of
i. a linear, branched, saturated or unsaturated, cyclic halo-alkyl or aryl group,
ii. a (meth)acrylate group, and
c. an oxidizing reagent.

The bis-DMTD derivative of any previous paragraph wherein the reaction product comprises, consists essentially of, consists of a compound of formula

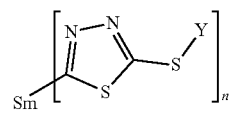

where
"m" is 1, 2 or 3, and "n" is 2; and
where "Y" is:
"R," a linear, branched, saturated or unsaturated, or cyclic $C_1$ to $C_{12}$, or $C_1$ to $C_{10}$, or $C_1$ to $C_8$, or even $C_1$ to $C_6$ alkyl or aryl group, or H;
"$CH_2CH[CH_3$ or $H]C(O)OZ$," where "Z" is H, or a $C_1$ to $C_{22}$ alkyl or aryl group.

The bis-DMTD derivative of any previous paragraph wherein "m" is 1 and "n" is 2.

The bis-DMTD derivative of any previous paragraph wherein "m" is 2 and "n" is 2.

The bis-DMTD derivative of any previous paragraph wherein "m" is 3 and "n" is 2.

The bis-DMTD derivative of any previous paragraph wherein "Y" is "R," a linear, branched, saturated or unsaturated, or cyclic $C_1$ to $C_{12}$, or $C_1$ to $C_{10}$, or $C_1$ to $C_8$, or even $C_1$ to $C_6$ alkyl or aryl group.

The bis-DMTD derivative of any previous paragraph wherein "Y" is H

The bis-DMTD derivative of any previous paragraph wherein "Y" is "$CH_2CH[CH_3$ or $H]C(O)OZ$," where "Z" is H, or a $C_1$ to $C_{22}$ alkyl or aryl group.

What is claimed is:
1. A DMTD derivative which is 2-(methylcarboxy-2-methylethyl)thio-5-thiol-1,3,4-thiadiazole.

\* \* \* \* \*